(12) United States Patent
Lee et al.

(10) Patent No.: US 11,439,754 B1
(45) Date of Patent: Sep. 13, 2022

(54) OPTIMIZING EMBEDDED FORMULATIONS FOR DRUG DELIVERY

(71) Applicant: Insulet Corporation, Acton, MA (US)

(72) Inventors: Joon Bok Lee, Acton, MA (US); Yibin Zheng, Hartland, WI (US); Jason O'Connor, Acton, MA (US); Ashutosh Zade, San Diego, CA (US)

(73) Assignee: INSULET CORPORATION, Acton, MA (US)

( * ) Notice: Subject to any disclaimer, the term of this patent is extended or adjusted under 35 U.S.C. 154(b) by 0 days.

(21) Appl. No.: 17/539,270

(22) Filed: Dec. 1, 2021

(51) Int. Cl.
*A61M 5/172* (2006.01)
*A61M 5/142* (2006.01)
*G16H 20/17* (2018.01)

(52) U.S. Cl.
CPC ...... *A61M 5/1723* (2013.01); *A61M 5/14244* (2013.01); *G16H 20/17* (2018.01); *A61M 2005/14208* (2013.01); *A61M 2230/201* (2013.01)

(58) Field of Classification Search
CPC ............ A61M 5/1723; A61M 5/14244; A61M 5/142; A61M 5/14248; A61M 5/31546; A61B 5/14532; A61B 5/4839; A61B 5/7275; G16H 20/17; G16H 20/10; G16H 50/20; G16H 40/63; G16H 50/50; A61K 9/007; A61K 38/28
See application file for complete search history.

(56) References Cited

U.S. PATENT DOCUMENTS

| | | |
|---|---|---|
| 303,013 A | 8/1884 | Horton |
| 2,797,149 A | 6/1957 | Skeggs |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |

(Continued)

FOREIGN PATENT DOCUMENTS

| AU | 2015301146 A1 | 3/2017 |
|---|---|---|
| CN | 1297140 A | 5/2001 |

(Continued)

OTHER PUBLICATIONS

US 5,954,699 A, 09/1999, Jost et al. (withdrawn)

(Continued)

*Primary Examiner* — Manuel A Mendez

(74) *Attorney, Agent, or Firm* — Goodwin Procter LLP

(57) ABSTRACT

Disclosed herein is a method for execution by a drug delivery device for determining an optimal dose of a liquid drug for current cycle of a medication delivery algorithm, the method utilizing a stepwise evaluation of a model and a cost function across a coarse search space consisting of coarse discrete quantities of the drug and a refined search space consisting of refined discrete quantities of the drug.

20 Claims, 3 Drawing Sheets

(56) References Cited

U.S. PATENT DOCUMENTS

| | | |
|---|---|---|
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,554,798 B1 | 4/2003 | Mann et al. |
| 6,556,850 B1 | 4/2003 | Braig et al. |

(56) References Cited

U.S. PATENT DOCUMENTS

| | | |
|---|---|---|
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |

(56) References Cited

U.S. PATENT DOCUMENTS

| | | |
|---|---|---|
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |

(56) References Cited

U.S. PATENT DOCUMENTS

| | | |
|---|---|---|
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2021/0050085 A1 | 2/2021 | Hayter et al. |
| 2021/0098105 A1 | 4/2021 | Lee et al. |

FOREIGN PATENT DOCUMENTS

| | | |
|---|---|---|
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 3607985 A1 | 2/2020 |
| GB | 2443261 A | 4/2008 |
| JP | S51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 05110601 A1 | 5/2004 |
| WO | 2004043250 A1 | 5/2004 |
| WO | 04092715 A1 | 10/2004 |
| WO | 2005051170 A2 | 6/2005 |
| WO | 2005113036 A1 | 12/2005 |
| WO | 2006053007 A2 | 5/2006 |
| WO | 2007064835 A2 | 6/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2010147659 A2 | 12/2010 |
| WO | 2011095483 A1 | 8/2011 |
| WO | 2012045667 A2 | 4/2012 |

(56) References Cited

FOREIGN PATENT DOCUMENTS

| | | |
|---|---|---|
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |

OTHER PUBLICATIONS

European Search Report for the European Patent Application No. 21168591.2, dated Oct. 13, 2021, 04 pages.
International Search Report and Written Opinion for the International Patent Application No. PCT/US2021/041954, dated Oct. 25, 2021, 13 pages.
International Search Report and Written Opinion for the International Patent Application No. PCT/US2021/047771, dated Dec. 22, 2021, 11 pages.
International Search Report and Written Opinion for the International Patent Application No. PCT/US2021/052855, dated Dec. 22, 2021, 11 pages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, dated Jun. 2, 2021, 15 pages.
Farkas et al. ""Single-Versus Triple-Lumen Central Catheter-Related Sepsis: A Prospective Randomized Study in a Critically Ill Population"" The American Journal of Medicine Sep. 1992 vol. 93 p. 277-282.
Davidson, Paul C., et al., A computer-directed intravenous insulin system shown to be safe, simple,and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A ""Microbial Contamination of Haemodialysis Catheter Connections"" Journal of Renal Care,European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al., "Multilumen Central Venous Catheters Increase Risk for Catheter-Related Bloodstream Infection: Prospective Surveillance Study".
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 dated Jul. 16, 2010.
International Search Report and Written Opinion in PCT/US2008/079641 dated Feb. 25, 2009.
Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al.,"Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP—Endocrinol Metab, vol. 294, E15-E26, first published Oct. 23, 2007.
International Preliminary Report on Patentability for the International Patent Application No. PCT/US2019/053603, dated Apr. 8, 2021, 9 pages.
International Search Report and Written Opinion for the International Patent Application No. PCT/US2019/053603, dated Jan. 7, 2020, 16 pages.

(56) References Cited

OTHER PUBLICATIONS

Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, dated May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, dated May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, dated May 27, 2021, 16 pages.
International Search Report and Written Opinion for the International Patent Application No. PCT/US2020/065226, dated May 31, 2021, 18 pages.
International Search Report and Written Opinion for the International Patent Application No. PCT/US2021/017659, dated May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, dated Dec. 13, 2017, 8 pages.
Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, dated May 16, 2017, 12 pages.
International Search Report and Written Opinion for the International Patent Application No. PCT/US2018/018901, dated Aug. 6, 2018, 12 pages.
International Search Report and Written Opinion for International Patent Application No. PCT/US2018/052467, dated Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/>. (Year:2017).
International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
International Search Report and Written Opinion for Application No. PCT/US2019/030652, dated Sep. 25, 2019, 19 pages.
International Search Report and Written Opinion for the International Patent Application No. PCT/US2020/052125, dated Aug. 12, 2020, 15 pages.
International Search Report and Written Opinion for the International Patent Application No. PCT/US2020/050332, dated Sep. 12, 2020, 12 pages.
European Patent Office, "Notification of Transmittal of the ISR and the Written Opinion of the International Searching Authority, or the Declaration," in PCT Application No. PCT/GB2015/050248, dated Jun. 23, 2015, 12 pages.
International Search Report and Written Opinion for the International Patent Application No. PCT/US2021/012246, dated Apr. 13, 2021, 15 pages.
International Search Report and Written Opinion for the International Patent Application No. PCT/US2021/013639, dated Apr. 28, 2021, 14 pages.
International Search Report and Written Opinion for the International Patent Application No. PCT/US2020/063326, dated May 3, 2021, 17 pages.

(56) References Cited

OTHER PUBLICATIONS

International Search Report and Written Opinion for International Patent Application No. PCT/US2021/051027, dated Jan. 7, 2022, 16 pages.
International Search Report and Written Opinion for International Patent Application No. PCT/US2021/052372, dated Jan. 26, 2022, 15 pages.
International Search Report and Written Opinion for the International Patent Application No. PCT/US2021/046607, dated Jan. 31, 2022, 20 pages.
International Search Report and Written Opinion for the International Patent Application No. PCT/US2021/055745, dated Feb. 14, 2022, 13 pages.
International Search Report and Written Opinion for the International Patent Application No. PCT/US2022/012896, dated Apr. 22, 2022, 15 pages.
International Search Report and Written Opinion for the International Patent Application No. PCT/US2022/013470, dated May 6, 2022, 14 pages.
International Search Report and Written Opinion for the International Patent Application No. PCT/US2022/013473, dated May 6, 2022, 13 pages.

OPTIMIZING EMBEDDED FORMULATIONS FOR DRUG DELIVERY

BACKGROUND

Many conventional automatic drug delivery systems are well known, including, for example, wearable drug delivery devices of the type shown in FIG. 2. The drug delivery device 102 can be designed to deliver any type of liquid drug to a user. In specific embodiments, the drug delivery device 102 can be, for example, an OmniPod® drug delivery device manufactured by Insulet Corporation of Acton, Mass. The drug delivery device 102 can be a drug delivery device such as those described in U.S. Pat. Nos. 7,303,549, 7,137,964, or U.S. Pat. No. 6,740,059, each of which is incorporated herein by reference in its entirety.

Wearable drug delivery devices 102 are typically configured with a processor and memory and are often powered by an internal battery or power harvesting device having limited amount of power available for powering the processor and memory. Further, because of the size of the device, the processing capability and memory for storage of software algorithms may also be limited. Due to these limitations, wearable drug delivery devices do not have an onboard medication delivery algorithm that determines, through a series of calculations based on feedback from sensors and other information, the timing and quantity of the liquid drug to be delivered to the user. Such medication delivery applications are typically found on a remote device, such as a remote personal diabetes manager (PDM) or a smartphone, for example, either of which being configured to transmit drug delivery instructions.

The medication delivery algorithm may use an optimization algorithm to periodically calculate the quantity of the liquid drug to be delivered to the user. For example, the medical delivery algorithm may operate, in one embodiment, on a 5-minute cycle. The optimization algorithm may utilize a mathematical glucose model and may minimize a cost function to determine the appropriate quantities of the liquid drug to be delivered. Such optimization algorithms often require a series of complex calculations with high computational and power consumption costs, making them difficult to implement in applications where only a low-power, efficient processing capability is available, such as in embedded applications. This is particularly important when it is desired to implement such optimization algorithms in disposable, small-scale electronics, such as a wearable drug delivery device 102.

Therefore, it would be desirable to provide a method to reduce the computational costs and power consumption for performing the optimization algorithm, to enable the medication delivery algorithm to reside onboard a wearable drug delivery device 102, and to enhance the life of the wearable drug delivery device 102 and the speed at which proper drug dosages can be calculated for delivery of the drug to the user or wearer of the wearable drug delivery device 102.

Definitions

As used herein, the term "liquid drug" should be interpreted to include any drug in liquid form capable of being administered by a drug delivery device via a subcutaneous cannula, including, for example, insulin, GLP-1, pramlintide, morphine, blood pressure medicines, chemotherapy drugs, fertility drugs or the like or co-formulations of two or more of GLP-1, pramlintide, and insulin.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In certain embedded, medical implementations, such as in a wearable drug delivery device 102, the precise solution to the optimization problem may not be required. This is largely due the fact that the difference in calculated doses for each cycle between an exact solution to the optimization problem and a close solution to the optimization problem may be below the minimum drug delivery resolution of the wearable drug delivery device 102. For example, in certain embodiments, the resolution of the delivery of the liquid drug may be limited to a fixed amount (e.g., 0.05 U, or 0.0005 mL). That is, the wearable drug delivery device 102 may only be capable of delivering the liquid drug in particular, discrete amounts. Therefore, an exact solution to the optimization problem providing a recommended dose that falls in between the particular, discrete amounts cannot be delivered, and, therefore, an approximation of the solution to the optimization problem is acceptable. Further, the differences between the calculated dose and the dose that the wearable drug delivery device 102 is capable of delivering to the user may not result in significant differences in the clinical outcome for the user. In some embodiments, the medication delivery algorithm may round the delivery to the nearest discrete amount capable of being delivered and add or subtract any differences to or from the calculated dose during the next cycle.

Therefore, the computational cost of executing the optimization algorithm can be greatly reduced (by 99%+) with a simple implementation of the optimization algorithm that allows the system to reach a solution that need not be accurate to the smallest decimal points but is sufficiently close so as to not impact the user's therapy.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

This disclosure presents various systems, components and methods for calculating a quantity of a liquid drug to be delivered to a user during a current execution cycle of a medication delivery algorithm. The embodiments described herein provide one or more advantages over conventional, prior art systems, components and methods, namely, a savings in power consumption and lower required processing power due to a simplified computational model used to solve the optimization problem.

Various embodiments of the present invention include systems and methods for delivering a medication to a user using a drug delivery device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be carried by the user or worn on the body of the user and that executes an algorithm that computes the times and dosages of delivery of the medication.

For example, the user device may execute an "artificial-pancreas" algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the drug delivery device or may be a separate device.

Alternatively, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the drug delivery device). In these embodiments, the drug delivery device contains computing hardware (e.g., a processor, memory, firmware, etc.) that executes some or all of the algorithm that computes the times and dosages of delivery of the medication.

Figure 1:
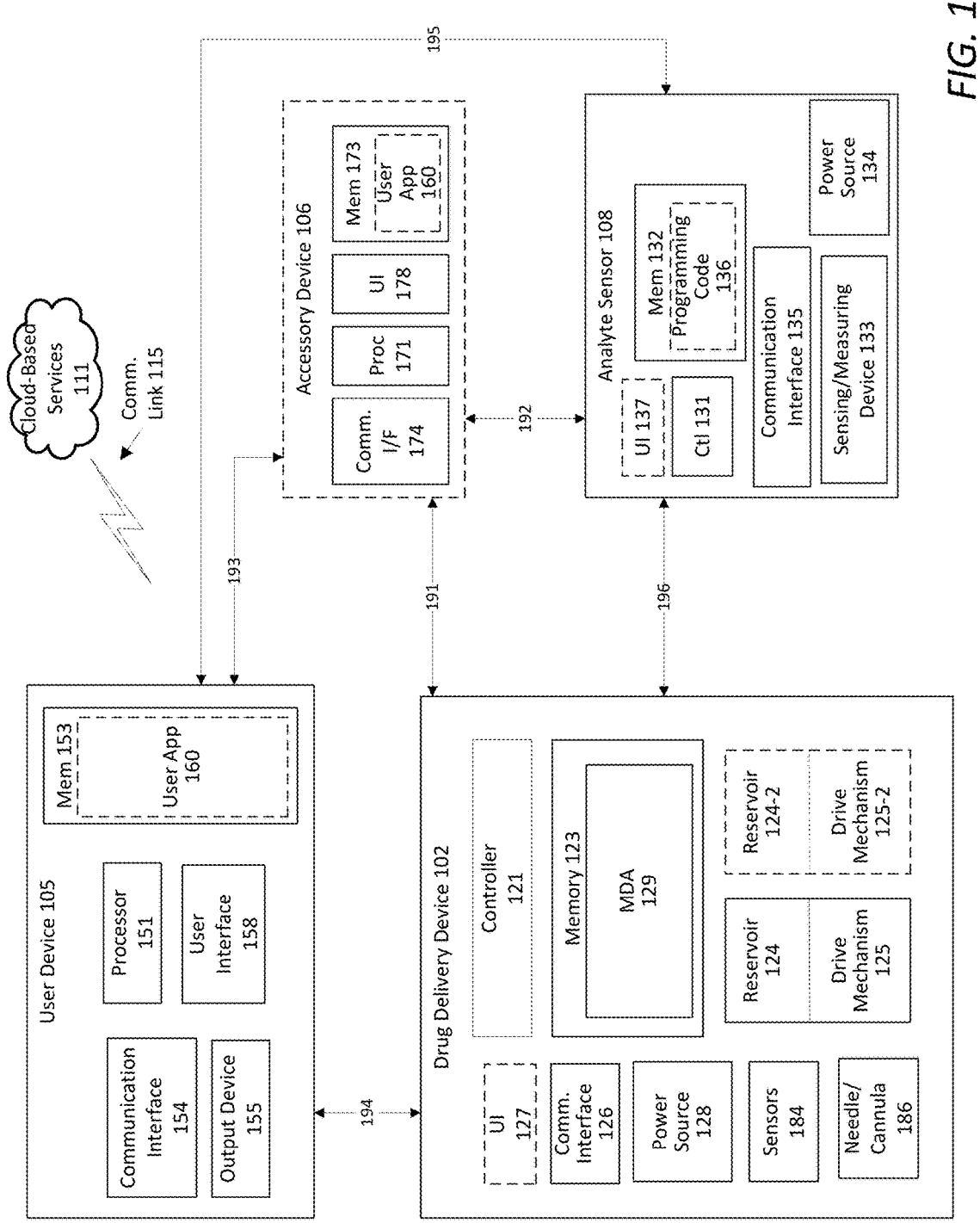
FIG. 1 illustrates a functional block diagram of an exemplary system suitable for implementing the systems and methods disclosed herein.
Figure 2:
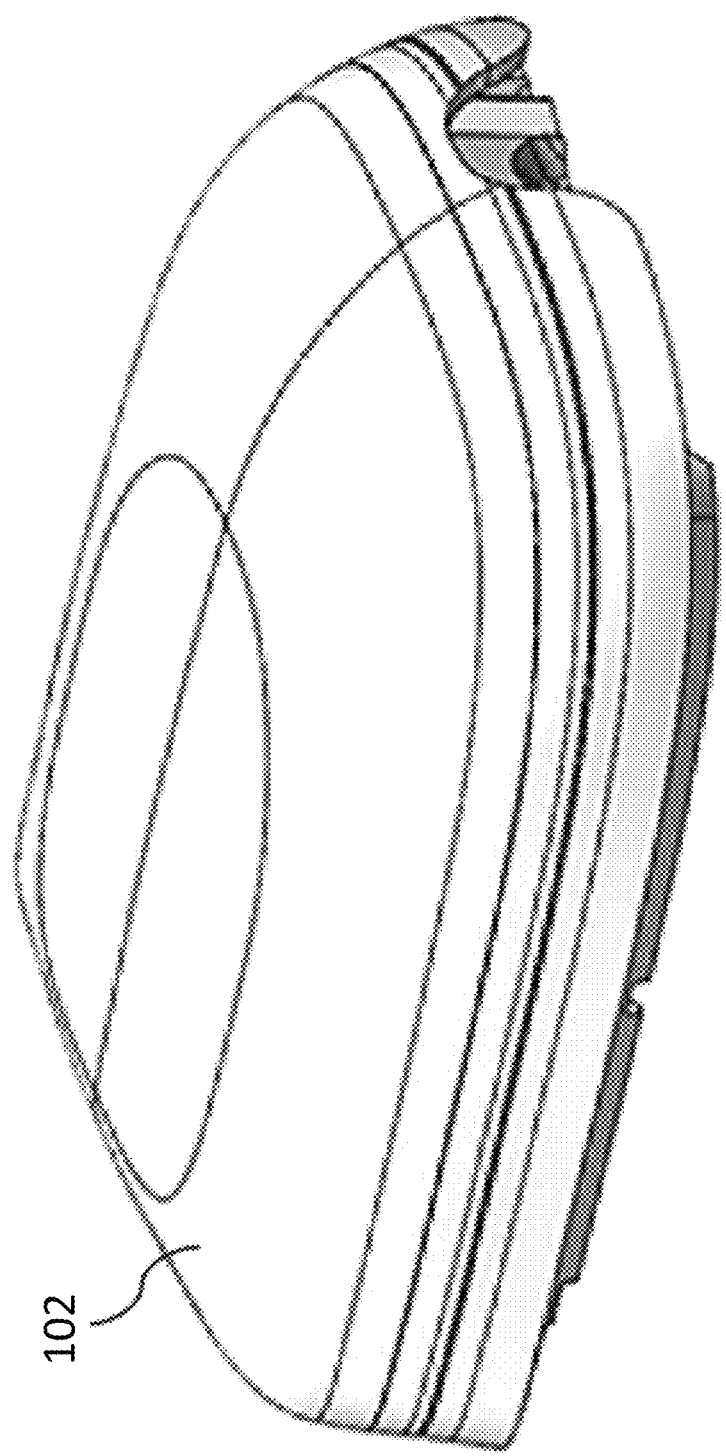
FIG. 2 is a depiction of a prior art wearable drug delivery device of the type in which the invention disclosed herein would be used.

FIG. 1 illustrates a functional block diagram of an exemplary drug delivery system 100 suitable for implementing the systems and methods described herein. The drug delivery system 100 may implement (and/or provide functionality for) a medication delivery algorithm, such as an artificial pancreas (AP) application, to govern or control the automated delivery of a drug or medication, such as insulin, to a user (e.g., to maintain euglycemia—a normal level of glucose in the blood). The drug delivery system 100 may be an automated drug delivery system that may include a drug delivery device 102 (which may be wearable), an analyte sensor 108 (which may also be wearable), and a user device 105.

Drug delivery system 100, in an optional example, may also include an accessory device 106, such as a smartwatch, a personal assistant device, or the like, which may communicate with the other components of system 100 via either a wired or wireless communication links 191-193.

User Device

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like, as discussed below. The user device 105 may be used to program, adjust settings, and/or control operation of drug delivery device 102 and/or the analyte sensor 108 as well as the optional smart accessory device 106.

The processor 151 may also be configured to execute programming code stored in device memory 153, such as the user app 160. The user app 160 may be a computer application that is operable to deliver a drug based on information received from the analyte sensor 108, the cloud-based services 111 and/or the user device 105 or optional accessory device 106. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an AP application, the processor 151 is also configured to execute a diabetes treatment plan (which may be stored in a memory) that is managed by user app 160. In addition to the functions mentioned above, when user app 160 is an AP application, it may provide further functionality to determine a carbohydrate-compensation dosage, a correction bolus dosage and determine a basal dosage according to a diabetes treatment plan. In addition, as an AP application, user app 160 provides functionality to output signals to the drug delivery device 102 via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

Drug Delivery Device

In various exemplary embodiments, drug delivery device 102 may include a reservoir 124 and drive mechanism 125, which are controllable by controller 121, executing a medication delivery algorithm (MDA) 129 stored in memory 123 onboard the drug delivery device (and in exemplary embodiments, a wearable drug delivery device). Alternatively, controller 121 may act to control reservoir 124 and drive mechanism 125 based on signals received from user app 160 executing on a user device 105 and communicated to drug delivery device 102 via communication link 194. Drive mechanism 125 operates to longitudinally translate a plunger through the reservoir, such as to force the liquid drug through an outlet fluid port to needle/cannula 186.

In an alternate embodiment, drug delivery device 102 may also include an optional second reservoir 124-2 and second drive mechanism 125-2 which enables the independent delivery of two different liquid drugs. As an example, reservoir 124 may be filled with insulin, while reservoir 124-2 may be filled with Pramlintide or GLP-1. In some embodiments, each of reservoirs 124, 124-2 may be configured with a separate drive mechanism 125, 125-2, respectively, which may be separately controllable by controller 121 under the direction of MDA 129. Both reservoirs 124, 124-2 may be connected to a common needle/cannula 186.

Drug delivery device 102 may be optionally configured with a user interface 127 providing a means for receiving input from the user and a means for outputting information to the user. User interface 127 may include, for example, light-emitting diodes, buttons on a housing of drug delivery device 102, a sound transducer, a micro-display, a microphone, an accelerometer for detecting motions of the device or user gestures (e.g., tapping on a housing of the device) or any other type of interface device that is configured to allow a user to enter information and/or allow drug delivery device 102 to output information for presentation to the user (e.g., alarm signals or the like).

Drug delivery device 102 includes a patient interface 186 for interfacing with the user to deliver the liquid drug. Patient interface 186 may be, for example, a needle or cannula for delivering the drug into the body of the user (which may be done subcutaneously, intraperitoneally, or intravenously). Drug delivery device 102 may further include a mechanism for inserting the needle/cannula 186 into the body of the user, which may be integral with or attachable to drug delivery device 102. The insertion mechanism may comprise, in one embodiment, an actuator that inserts the needle/cannula 186 under the skin of the user and thereafter retracts the needle, leaving the cannula in place.

In one embodiment, drug delivery device 102 includes a communication interface 126, which may be a transceiver that operates according to one or more radio-frequency protocols, such as Bluetooth®, Wi-Fi, near-field communication, cellular, or the like. The controller 121 may, for example, communicate with user device 105 and an analyte sensor 108 via the communication interface 126.

In some embodiments, drug delivery device 102 may be provided with one or more sensors 184. The sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between the patient interface 186 and reservoir 124. The pressure sensor may be coupled to or integral with the actuator for inserting the patient interface 186 into the user. In an example, the controller 121 may be operable to determine a rate of drug infusion based on the indication of the fluid pressure. The rate of drug infusion may be compared to an infusion rate threshold, and the comparison result may be usable in determining an amount of insulin onboard (JOB) or a total daily insulin (TDI) amount. In one embodiment, analyte sensor 108 may be integral with drug delivery device 102.

Drug delivery device 102 further includes a power source 128, such as a battery, a piezoelectric device, an energy harvesting device, or the like, for supplying electrical power to controller 121, memory 123, drive mechanisms 125 and/or other components of drug delivery device 102.

Drug delivery device 102 may be configured to perform and execute processes required to deliver doses of the medication to the user without input from the user device 105 or the optional accessory device 106. As explained in more detail, MDA 129 may be operable, for example, to determine an amount of insulin to be delivered, JOB, insulin remaining, and the like, and to cause controller 121 to activate drive mechanism 125 to deliver the medication from reservoir 124. MDA 129 may take as input data received from the analyte sensor 108 or from user app 160.

The reservoirs 124, 124-2 may be configured to store drugs, medications or therapeutic agents suitable for automated delivery, such as insulin, Pramlintide, GLP-1, co-formulations of insulin and GLP-1, morphine, blood pressure medicines, chemotherapy drugs, fertility drugs or the like.

Drug delivery device 102 may be a wearable device and may be attached to the body of a user at an attachment location and may deliver any therapeutic agent, including any drug or medicine, such as insulin or the like, to a user at or around the attachment location. A surface of drug delivery device 102 may include an adhesive to facilitate attachment to the skin of a user.

When configured to communicate with an external device, such as the user device 105 or the analyte sensor 108, drug delivery device 102 may receive signals over the wired or wireless link 194 from the user device 105 or from the analyte sensor 108. The controller 121 of drug delivery device 102 may receive and process the signals from the respective external devices as well as implementing delivery of a drug to the user according to a diabetes treatment plan or other drug delivery regimen.

Accessory Device

Optional accessory device 107 may be a wearable smart device, for example, a smart watch (e.g., an Apple Watch®), smart eyeglasses, smart jewelry, a global positioning system-enabled wearable, a wearable fitness device, smart clothing, or the like. Similar to user device 105, the accessory device 107 may also be configured to perform various functions including controlling drug delivery device 102. For example, the accessory device 107 may include a communication interface 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the user app 160, or a pared-down version of user app 160 with reduced functionality. In some instances, accessory device 107 may also include sensors of various types.

Analyte Sensor

The analyte sensor 108 may include a controller 131, a memory 132, a sensing/measuring device 133, an optional user interface 137, a power source/energy harvesting circuitry 134, and a communication interface 135. The analyte sensor 108 may be communicatively coupled to the processor 151 of the management device 105 or controller 121 of drug delivery device 102. The memory 132 may be configured to store information and programming code 136.

The analyte sensor 108 may be configured to detect multiple different analytes, such as glucose, lactate, ketones, uric acid, sodium, potassium, alcohol levels or the like, and output results of the detections, such as measurement values or the like. The analyte sensor 108 may, in an exemplary embodiment, be a continuous glucose monitor (CGM) configured to measure a blood glucose value at a predetermined time interval, such as every 5 minutes, every 1 minute, or the like. The communication interface 135 of analyte sensor 108 may have circuitry that operates as a transceiver for communicating the measured blood glucose values to the user device 105 over a wireless link 195 or with drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 121 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from drug delivery device 102, in various embodiments, the analyte sensor 108 and drug delivery device 102 may be incorporated into the same unit. That is, in various examples, the analyte sensor 108 may be a part of and integral with drug delivery device 102 and contained within the same housing as drug delivery device 102 or in a housing attachable to the housing of drug delivery device 102 or otherwise adjacent thereto. In such an example configuration, the controller 121 may be able to implement the functions required for the proper delivery of the medication alone without any external inputs from user device 105, the cloud-based services 111, another sensor (not shown), the optional accessory device 106, or the like.

Cloud-Based Services

Drug delivery system 100 may communicate with or receive services from cloud-based services 111. Services provided by cloud-based services 111 may include data storage that stores personal or anonymized data, such as blood glucose measurement values, historical IOB or TDI, prior carbohydrate-compensation dosage, and other forms of data. In addition, the cloud-based services 111 may process anonymized data from multiple users to provide generalized information related to TDI, insulin sensitivity, IOB and the like. The communication link 115 that couples the cloud-based services 111 to the respective devices 102, 105, 106, 108 of system 100 may be a cellular link, a Wi-Fi link, a Bluetooth® link, or a combination thereof.

Communication Links

The wireless communication links 115 and 191-196 may be any type of wireless link operating using known wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 126, 135, 154 and 174.

Operational Example

In an operational example, user application 160 implements a graphical user interface that is the primary interface with the user and is used to start and stop drug delivery device 102, program basal and bolus calculator settings for manual mode as well as program settings specific for automated mode (hybrid closed-loop or closed-loop).

User app 160, provides a graphical user interface 158 that allows for the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

User app 160 may configured to operate in a manual mode in which user app 160 will deliver insulin at programmed basal rates and bolus amounts with the option to set basal profiles for different times of day or temporary basal profiles. The controller 121 will also have the ability to function as a sensor-augmented pump in manual mode, using sensor glucose data provided by the analyte sensor 108 to populate the bolus calculator.

User app 160 may be configured to operate in an automated mode in which user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

The user app 160 (or MDA 129) may provide periodic insulin micro-boluses based upon past glucose measurements and/or a predicted glucose over a prediction horizon (e.g., 60 minutes). Optimal post-prandial control may require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

In some embodiments, user device 105 and the analyte sensor 108 may not communicate directly with one another. Instead, data (e.g., blood glucose readings) from analyte sensor may be communicated to drug delivery device 102 via link 196 and then relayed to user device 105 via link 194. In some embodiments, to enable communication between analyte sensor 108 and user device 105, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (IOB). IOB is estimated by user app 160 taking into account any manual bolus and insulin delivered by the algorithm, and IOB may be divided between a basal IOB and a bolus IOB, the basal IOB accounting for insulin delivered by the algorithm, and the bolus IOB accounting for any bolus deliveries.

Description of Embodiments

The primary embodiment of the invention is directed to a method for simplifying an optimization algorithm used in the calculation of quantities of a liquid drug, for example, insulin, to be periodically delivered to a user by a wearable drug delivery device 102. In the primary embodiment, rather than executing an optimization algorithm with a high computational cost, a simple stepwise exploration across all possible search spaces can be performed to bound the total computational cost and allow the calculations to be executed in embedded form.

A typical control algorithm can utilize a model of the system to be controlled to predict the outputs of the proposed drug dose. The model can be used to determine the best dose to be given to the user. For example, in an insulin delivery system, the user's glucose can be modeled as a recursive model of past glucose and insulin delivery values. Although, as would be realized by one of skill in the art, any such model can be used, one such model can be expressed by Eq. (1) as:

$$G(k)=K \cdot I(k-3)+b_1 G(k-1)+b_2 G(k-2)+b_3 G(k-3)+ \quad (1)$$

where:
k is the current cycle for which the glucose is being modelled;
K is a gain factor;
$b_1, b_2, b_3 \ldots$ are weights for each cycle of MDA 129; and
G is the estimated glucose for the current cycle, k.

The glucose model can be run recursively to predict glucose levels for future cycles. For each series of proposed insulin doses I(k+N) in the next N number of cycles, different glucose trajectory over those cycles G (k+N) can be calculated. Then, the total value of this projected insulin dose and glucose trajectory can be calculated by calculating a standard cost function, such as the exemplary cost expressed by Eq. (2) as:

$$J(k) = Q \sum_{i=1}^{N} G(k+i)^2 + R \sum_{i=1}^{n} I(k+i)^2 \quad (2)$$

where:
the left term with coefficient Q is the cost of the glucose deviations from a glucose setpoint; and
the right term with coefficient R is the cost of the insulin deviations from a particular basal rate.

Again, as would be a realized by one of skill in the art, any cost function may be used. An exemplary cost function is described in detail in U.S. patent application Ser. No. 16/789,051 (U.S. Published Patent Application No. 2021/0244881).

In certain embodiments, the glucose deviation and insulin delivery cost can be executed in various ways, such as by calculating the deviations against a specific target (such as a glucose control setpoint and basal insulin delivery) and the deviations can be calculated for various orders, such as quadratic or higher powers.

In typical applications, the calculation of the cost for each possible glucose and insulin trajectory, and determining the trajectories with a minimum cost, can be performed by optimization algorithms with high computational cost. However, as explained in the Summary above, in many medical applications, the high computational cost optimization algorithms are not necessary.

This is particularly the case in insulin delivery applications, as a typical minimum resolution of insulin pumps (e.g., 0.05 U) and variations in the timing of each dose being delivered within a short time window does not result in significant changes in the user's overall glucose outcomes.

Figure 3:
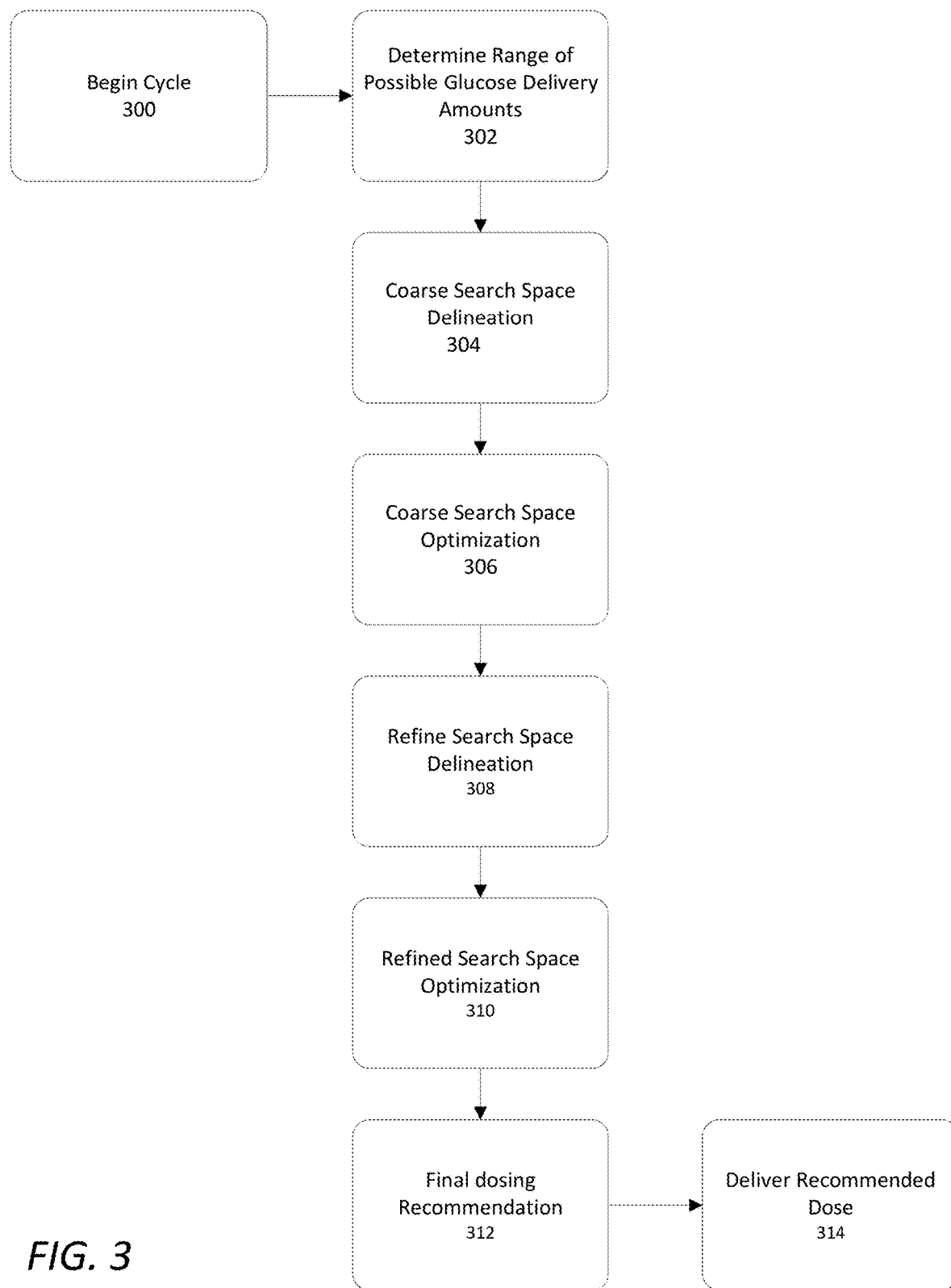
FIG. 3 is a flowchart showing the steps comprising the disclosed method.

The stepwise algorithm executed across all possible search spaces will now be explained and is shown in flowchart form in FIG. 3. In step 302 of the stepwise algorithm, the range of possible glucose delivery amounts for the current cycle is determined. Typically, the lower end of the range will be 0.0 as MDA 129 has the option, during any cycle, to cause or recommend that no dose be delivered. The upper range or limit of the possible glucose delivery amounts may be constrained by safety constraints built in the MDA 129 to prevent excess insulin from being delivered, or for any other reason. For example, in one embodiment, the delivery range can be set between 0.0 U and 0.6 U per cycle. For purposes of explanation of the disclosed method, this exemplary range will be used.

At step 304, the range is delineated into a coarse search space comprising coarse discrete quantities. For example, in the exemplary range of 0 U to 0.6 U, the search space may be delineated into 0.1 U coarse discrete quantities. Thus, the coarsely delineated search space would be delineated as: 0.0 U, 0.1 U, 0.2 U, 0.3 U, 0.4 U, 0.5 U, and 0.6 U. As would be realized by one of skill in the art, any coarse discrete quantities may be used to delineate the range, granted that they are indeed coarse relative to the minimum delivery resolution of the drug delivery device.

At step 306, the coarse search space is optimized. The search space can initially be narrowed by determining the coarse optimal insulin delivery. Specifically, all insulin delivery rates in the next N cycles can be set at a fixed value, at the coarse discrete quantities within the search space, and the corresponding glucose trajectories can be calculated.

In the explanatory example, the recursive model expressed by Eq. (1) can be calculated 7 times, each time assuming that I(k+1) . . . I(k+N) is calculated for each quantity in the coarse search space. Then, the corresponding costs can be calculated based on a cost function, an example of which is expressed by Eq. (2). In the explanatory example, this results in the following exemplary calculations:

| I(k + 1) . . . I(k + N) | 0.0 | 0.1 | 0.2 | 0.3 | 0.4 | 0.5 | 0.6 |
|---|---|---|---|---|---|---|---|
| J | 1300 | 1100 | 800 | 750 | 760 | 770 | 800 |

As can be seen, in accordance with the exemplary model and cost function, a glucose delivery of 0.3 U in the next cycle produces the lowest cost.

At step 308, the coarse delineation of the search space is refined. The search space is narrowed to a smaller area around the coarse discrete quantity with a lowest cost (in the explanatory example, 0.3 U). In the second, refined delineation of the search space, the first insulin delivery (i.e., I(k+1)) search space can be divided into finer increments, centered around the coarse discrete quantity with a lowest cost, to provide more detailed resolution of the actual insulin delivery to be provided to the user. The search space for the remaining data sets (i.e., I(k+2) . . . I (k=N)) can be evaluated using the coarse discrete quantities.

In the explanatory example, the search space has been narrowed and centered around 0.3 U. Therefore, the first projected insulin delivery can be defined to be between 0.2 u and 0.4 U in a finer increment (e.g., 0.025 U) and the remaining projected insulin deliveries can be defined to be between 0.2 U and 0.4 U in a similar increment or in a coarser increment (e.g., 0.05 U), but preferably in a coarser increment to reduce computational requirements. As would be realized by one of skill in the art, the finer increment can be any desired quantity, while the range can be any range, preferably centered around the coarse solution with the minimal cost. At step 310, the refined search space can be optimized. In the explanatory example, the calculations could produce the following results:

| I(k + 1) | I(k + 2) ... 1(k + N) | J |
|---|---|---|
| 0.2 | 0.2 | 800 |
|  | 0.25 | 795 |
|  | 0.3 | 780 |
|  | 0.35 | 775 |
|  | 0.4 | 770 |
| 0.225 | 0.2 | 765 |
|  | 0.25 | 775 |
|  | 0.3 | 760 |
|  | 0.35 | 765 |
|  | 0.4 | 770 |
| ... | ... |  |
| 0.375 | 0.2 | 760 |
|  | 0.25 | 756 |
|  | 0.3 | 755 |
|  | 0.35 | 758 |
|  | 0.4 | 756 |
| 0.4 | 0.2 | 758 |
|  | 0.25 | 759 |
|  | 0.3 | 760 |
|  | 0.35 | 762 |
|  | 0.4 | 763 |

As can be seen, in the explanatory example, only 52 total calculations were required. This includes 7 calculations in the coarse search space optimization step 306 and 45 calculations in the refined search space optimization step 310 (9 [0.2, 0.225, 0.25, 0.275, 0.3, 0.325, 0.35, 0.375, 0.4]×5[0.2, 0.25, 0.3, 0.35, 0.4]). In other embodiments, wherein different intervals and ranges have been selected, the total number of calculations required in both steps 306 and 310 may change; however, the stepwise exploration of the coarse and refined search spaces is much more computationally efficient than running a conventional more computationally expensive optimization algorithm.

Finally, at step 312, the recommended insulin dose is finalized. The solution that provides a minimal cost in the second, refined search space can be provided as the recommended insulin delivery trajectory. In the explanatory example, as can be seen, the lowest calculation of the cost function occurs in the 0.375 interval, therefore, the recommended insulin delivery dose for the current cycle would be 0.375 U. At 314, the recommended dose is delivered by drug delivery device 102 to the user, as explained above.

Note that, if the recommended dose does not fall within the resolution of the drug delivery device 102, then the actual dose delivered may be rounded up or down to the nearest discrete increment that the drug delivery device 102 is capable of delivering, based on the resolution. Any remainder falling in between the incremental discrete resolutions of the drug delivery device 102 may be added to or subtracted from the recommended dose for the next cycle.

The above process is repeated for each cycle of MDA 129. In one embodiment, MDA 129 may execute a cycle every 5 minutes, although other intervals may be selected.

As previously mentioned, it is important to note that the various search spaces and resolution parameters used by the disclosed method can be widely tunable. For example, the coarse spacing calculations could be reduced to 0.2 U rather than 0.1 U resolution, as used in the explanatory example.

Overall, the disclosed method results in significantly less iterations of the calculation of the glucose model and the cost function. The 52 calculations provided in the explanatory example is significantly less calculation burdensome than a typical optimization algorithm, with a wide and multivariate search space. The resolution of the drug does recommendation is still within the resolution of the drug delivery mechanism.

The following examples pertain to various embodiments of the systems and methods disclosed herein for providing a method for determining an optimal delivery of a drug by providing a stepwise exploration of a search space of possible quantities of the drug to be delivered to the user.

Example 1 is a method comprising the steps of defining a core search space, evaluating a model and cost function for each discrete quantity in the core search space, defining a refined search space, evaluating the model and cost function over the refined search space and selecting the refined discrete quantity having the lowest cost is the recommended dose of the drug.

Example 2 is an extension of Example 1, or any other example disclosed herein, base uses discrete quantities which are smaller than the discrete quantities used in the course search space.

Example 3 is an extension of Example 1, or any other example disclosed herein, wherein refined search space is smaller than the core search space.

Example 4 is an extension of Example 1, or any other example disclosed herein, wherein the range of possible doses of the drug ranges from zero to a maximum quantity determined by the medication delivery algorithm.

Example 5 is an extension of Example 4, or any other example disclosed herein, wherein the maximum quantity is dependent upon safety constraints built into the medication delivery algorithm.

Example 6 is an extension of Example 1, or any other example disclosed herein, wherein the drug is insulin delivered by a wearable drug delivery device.

Example 7 is an extension of Example 6, or any other example disclosed herein, wherein the model was a recursive glucose model used to predict glucose levels of the user in a predetermined number of future cycles based on the delivery of a particular quantity of insulin.

Example 8 is an extension of Example 7, or any other example disclosed herein, wherein the cost function calculates the cost for each possible glucose and insulin trajectory and determines a trajectory with the lowest cost.

Example 9 is an extension of Example 8, or any other example disclosed herein, wherein the cost function is based on glucose deviations and insulin deliveries wherein the glucose deviations are calculated against a specific target.

Example 10 is a system comprising a processor and software implementing a medication delivery algorithm executed by the processor, the software determining a recommended dose for drug for a current cycle of medication delivery algorithm by performing the functions of defining a core search space, evaluating a model and cost function for each discrete quantity in the core search space, defining a refined search space, evaluating the model and cost function over the refined search space and selecting the refined discrete quantity having the lowest cost is the recommended dose of the drug.

Example 11 is an extension of Example 10, or any other example disclosed herein, further comprising a drug delivery device for delivering the recommended dose of the drug to the user.

Example 12 is an extension of Example 11, or any other example disclosed herein, wherein the processor and software or integral with the drug delivery device.

Example 13 is an extension of Example 10, or any other example disclosed herein, wherein the refined discrete quantities are smaller than the course discrete quantities.

Example 14 is an extension of Example 10, or any other example disclosed herein, wherein the refined search space is smaller than the coarse search space Example 15 is an extension of Example 10, or any other example disclosed herein, wherein the range of possible doses of the drug ranges from zero to a maximum quantity determined by the medication delivery algorithm.

Example 16 is extension of Example 15, or any other example disclosed herein, wherein the maximum quantity is dependent upon safety constraints built into the medication delivery algorithm.

Example 17 is an extension of Example 11, or any other example disclosed herein, wherein the drug is insulin delivered by the wearable drug delivery device.

Example 18 is an extension of Example 17, or any other example disclosed herein, wherein the model is a recursive glucose model used to predict glucose levels of the user in a predetermined number of future cycles based on delivery of a particular quantity of insulin.

Example 19 is an extension of example 18, or any other example disclosed herein, wherein the cost function calculates the cost for each possible glucose and insulin trajectory and determines a trajectory with a lowest cost.

Example 20 is an extension of Example 19, or any other example disclosed herein, wherein the cost function is based on glucose deviations and insulin delivery deviations, wherein the glucose deviations are calculated against the specific target.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

To those skilled in the art to which the invention relates, many modifications and adaptations of the invention may be realized. Implementations provided herein, including values of tunable parameters, should be considered exemplary only and are not meant to limit the invention in any way. As one of skill in the art would realize, many variations on implementations discussed herein which fall within the scope of the invention are possible. Moreover, it is to be understood that the features of the various embodiments described herein were not mutually exclusive and can exist in various combinations and permutations, even if such combinations or permutations were not made express herein, without departing from the spirit and scope of the invention. Accordingly, the method and apparatus disclosed herein are not to be taken as limitations on the invention but as an illustration thereof. The scope of the invention is defined by the claims which follow.

The invention claimed is:

1. A method of determining a dose of a drug for a current cycle of a medication delivery algorithm in an automated drug delivery system comprising:
    defining a first coarse search space by coarsely delineating a range of possible doses of the drug into coarse discrete quantities;
    evaluating a model and a cost function for the current cycle and a predetermined number of future cycles for each coarse discrete quantity in the first coarse search space;
    defining a refined search space by delineating, into refined discrete quantities, a range of doses of the drug centered around the coarse discrete quantity having the lowest cost, the refined search space having a finer delineation than the first coarse search space;
    evaluating the model and the cost function for the current cycle and the predetermined number of future cycles, wherein the current cycle is evaluated over the refined search space and the predetermined number of future cycles are evaluated over a second coarse search space; and
    selecting the refined discrete quantity having the lowest cost as the recommended dose of the drug.

2. The method of claim 1 wherein the refined discrete quantities are smaller than the coarse discrete quantities.

3. The method of claim 1 wherein the refined search space is smaller than the first coarse search space.

4. The method of claim 1 wherein the range of possible doses of the drug ranges from 0 to a maximum quantity determined by the medication delivery algorithm.

5. The method of claim 4 wherein the maximum quantity is dependent upon safety constraints built into the medication delivery algorithm.

6. The method of claim 1 wherein the drug is insulin delivered by a wearable drug delivery device.

7. The method of claim 6 wherein the model is a recursive glucose model used to predict glucose levels of the user in a predetermined number of future cycles based on delivery of a particular quantity of insulin.

8. The method of claim 7 wherein the cost function calculates the cost for each possible glucose and insulin trajectory and determines the trajectory with a lowest cost.

9. The method of claim 8 wherein the cost function is based on glucose deviations and insulin delivery deviations, wherein the glucose deviations are calculated against a specific target.

10. A system comprising:
    a processor;
    software implementing a medication delivery algorithm, executed by the processor, the software determining a recommended dose of a drug for a current cycle of the medication delivery algorithm by performing the functions of:
        defining a first coarse search space by coarsely delineating a range of possible doses of the drug into coarse discrete quantities;
        evaluating a model and a cost function for the current cycle and a predetermined number of future cycles for each coarse discrete quantity in the first coarse search space;
        defining a refined search space by delineating, into refined discrete quantities, a range of doses of the drug centered around the coarse discrete quantity having the lowest cost, the refined search space having a finer delineation than the first coarse search space;

evaluating the model and the cost function for the current cycle and the predetermined number of future cycles, wherein the current cycle is evaluated over the refined search space and the predetermined number of future cycles are evaluated over the second coarse search space; and selecting the refined discrete quantity having the lowest cost as the recommended dose of the drug.

11. The system of claim 10 further comprising:
a drug delivery device for delivering the recommended dose of the drug to the user.

12. The system of claim 11 wherein the processor and software are integral with the drug delivery device.

13. The system of claim 10 wherein the refined discrete quantities are smaller than the coarse discrete quantities.

14. The system of claim 10 wherein the refined search space is smaller than the first coarse search space.

15. The system of claim 10 wherein the range of possible doses of the drug ranges from 0 to a maximum quantity determined by the medication delivery algorithm.

16. The system of claim 15 wherein the maximum quantity is dependent upon safety constraints built into the medication delivery algorithm.

17. The system of claim 11 wherein the drug is insulin delivered by the wearable drug delivery device.

18. The system of claim 17 wherein the model is a recursive glucose model used to predict glucose levels of the user in a predetermined number of future cycles based on delivery of a particular quantity of insulin.

19. The system of claim 18 wherein the cost function calculates the cost for each possible glucose and insulin trajectory and determines the trajectory with a lowest cost.

20. The system of claim 19 wherein the cost function is based on glucose deviations and insulin delivery deviations, wherein the glucose deviations are calculated against a specific target.

* * * * *